United States Patent [19]

Armstead

[11] Patent Number: 4,943,286
[45] Date of Patent: * Jul. 24, 1990

[54] PATIENT UNDERPAD

[76] Inventor: Kenneth W. Armstead, P.O. Box 598, Lebanon, Tenn. 37087

[*] Notice: The portion of the term of this patent subsequent to Sep. 20, 2005 has been disclaimed.

[21] Appl. No.: 292,092

[22] Filed: Dec. 30, 1988

[51] Int. Cl.⁵ .............................................. A61F 13/16
[52] U.S. Cl. ..................................... 604/558; 604/365
[58] Field of Search ........................ 604/358, 367, 365

[56] References Cited

U.S. PATENT DOCUMENTS

| | | | |
|---|---|---|---|
| 3,901,240 | 8/1975 | Hoey | 604/365 X |
| 4,011,871 | 3/1977 | Taft | 604/369 X |
| 4,541,426 | 9/1985 | Webster | 128/156 |
| 4,753,840 | 6/1988 | Van Gompel | 604/365 X |
| 4,767,825 | 8/1988 | Pazos et al. | 604/366 |
| 4,772,281 | 9/1988 | Armsted | 604/358 |
| 4,788,972 | 12/1988 | De Busk | 604/358 X |
| 4,813,944 | 3/1989 | Haney et al. | 604/358 |

FOREIGN PATENT DOCUMENTS

| | | | |
|---|---|---|---|
| EP 88738 | 9/1983 | European Pat. Off. | 604/358 |
| 3316431 | 11/1984 | Fed. Rep. of Germany | 604/358 |

*Primary Examiner*—Richard J. Apley
*Assistant Examiner*—Rachel M. Healey
*Attorney, Agent, or Firm*—Mark J. Patterson

[57] ABSTRACT

An absorbent re-usable patient underpad is formed of four layers of fabric comprisig from to top bottom: a polyester-rayon needle form non-woven fabric, non-woven polyester; thermoplastic unrethane; and a synthetic fleece warpknit fabric. The first layer is placed through an iron and heated to temperatures substantially at 380 to 400 degrees F. the second, third, and fourth layers are bonded together.

5 Claims, 1 Drawing Sheet

PATIENT UNDERPAD

BACKGROUND OF THE INVENTION

This invention relates generally to an absorbent pad for use in hospitals and nursing homes and more particularly to an improved absorbent pad for use in hospitals and nursing homes beneath the patients who are incontinent or who might otherwise have a need for an absorbent and protective component of their bedding.

It will be appreciated by those skilled in the art that the problem of incontinence in seriously ill or elderly patients at home, in hospitals, and in nursing homes is well recognized. To this end, many products have been developed and marketed for use in protecting patient's bedding from damage caused by absorption of urine and other fluids. However, minimizing patient irritation and discomfort caused by prolonged exposure to absorb fluids is also a concern of those caring for the patient.

Disposable underpads are currently used by many institutions but are relatively expensive and do not provide optimum comfort and absorption because of the types of materials that must be used. Re-usable underpads previously known in the industry suffer from any number of draw backs. The most significant problem in re-usable pads currently available is durability, that is, ability to withstand exposure to soap, bleach, and high temperatures of wash and dry cycles. Currently available pads will suffer significant breakdown after 100 washings or less. Wrinkling of the pads over time is also a problem.

U.S. Pat. No. 4,772,281 issued to K. Armstead on Sept. 20, 1988, discloses an improved patient underpad that does not breakdown after repeated washings. The pad disclosed by that invention successfully stood up to 300 washings or more. However, after use and experimentation with this pad, it was found that the pad could become rougher over time. This rough texture created discomfort by some users. This roughness is caused by a top layer of the fabric being an absorbent rayon-polyester blend that is not heat-treated. Therefore, the '281 pad included a top layer of woven polyester or polyester tricot mesh to provide a smooth patient contact surface. 19 However, this adds to the expense in manufacturing the pad, due to the extra layer of fabric and the need for bonding it to the second absorbent layer.

Finally, it has also been discovered that further improvements in the chemical and heat tolerance of the water barrier layer of the pad can be made by using a urethane-based barrier.

SUMMARY OF THE INVENTION

In the present invention, a washable and reusable patient underpad is formed of four separate layers: a top layer (patient-contact) of absorbent polyester-rayon needle form non-woven fabric; a second layer of non-woven polyester; a third layer of synthetic water impervious material; and a fourth layer of synthetic fleece warp knit fabric. The second, third and fourth layers are bonded together. The top layer is run through a hot iron at a temperature of approximately 350 degrees to 380 degrees F. All layers are then stitched together around the top and bottom outside edges. This novel combination of fabrics, ironing, and bonding overcomes the disadvantages and problems of the prior art.

The top layer of polyester-rayon needle form non-woven fabric when run through a hot iron, creates a surface that does not rough up even after repeated washing and drying. The pad withstands dryer heat and bleach better than cotton, nylon, or woven polyester or polyester tricot mesh.

The top layer is also the "soaker" or primary fluid absorbent layer. Rayon is an excellent absorbent material. The polyester acts as a stabilizer for the rayon which will not hold up as well if unblended. It also is a faster drying fabric combination than many "soaker" fabrics used in the prior art.

The second layer of non-woven polyester adds strength to the pad for durability and repeated washings and, by bonding this layer to the water barrier layer below it, the barrier is protected from bonding to itself when exposed to the high temperature of commercial dryers. It also holds up to heat and bleach better than nylon.

The third layer of synthetic material serves as a liquid barrier between the soaker layer and the bedding. It will last longer and is easier to work with during manufacturing than rubber and similar fabrics. In the preferred embodiment, the third water barrier layer will comprise two separate films of thermoplastic urethane ester heat bonded to a middle film of thermoplastic urethane ether.

The bottom layer of synthetic fleece warpknit fabric is so closely wound that it is almost water proof. This minimizes the effects of the detergent on the third water barrier layer. It is also smoother than fabrics now commonly used as the bottom layer for underpads. This makes it easier to slide the pad on the bedding when moving or turning the patient.

The principal object of the present invention, then, is to provide a reasonable patient underpad which is suitable for use in nursing homes, hospitals, and other institutions in the care of incontinent patients.

A further object of the invention is to provide a reasonably low cost underpad which can withstand numerous wash and dry cycles with a minimum of damage to and wrinkling of the pad.

Another object of the present invention is to provide a re-usable underpad which can be washed and dried commercially at least 200 to 300 times before it must be replaced.

Another object of the present invention is to provide an underpad which will absorb and hold larger amounts of fluid while minimizing discomfort to the patient and while protecting the surrounding environment from damage.

Another object of the present invention is to provide an absorbant underpad which will dry quickly after washing.

Another object of the present invention is to provide a top surface which will not rough-up after numerous washings and drying.

A further object of the invention is to provide smooth top and bottom surfaces for patient comfort and for ease in moving the patient on the bed.

DESCRIPTION OF PREFERRED EMBODIMENT

Figure 1:
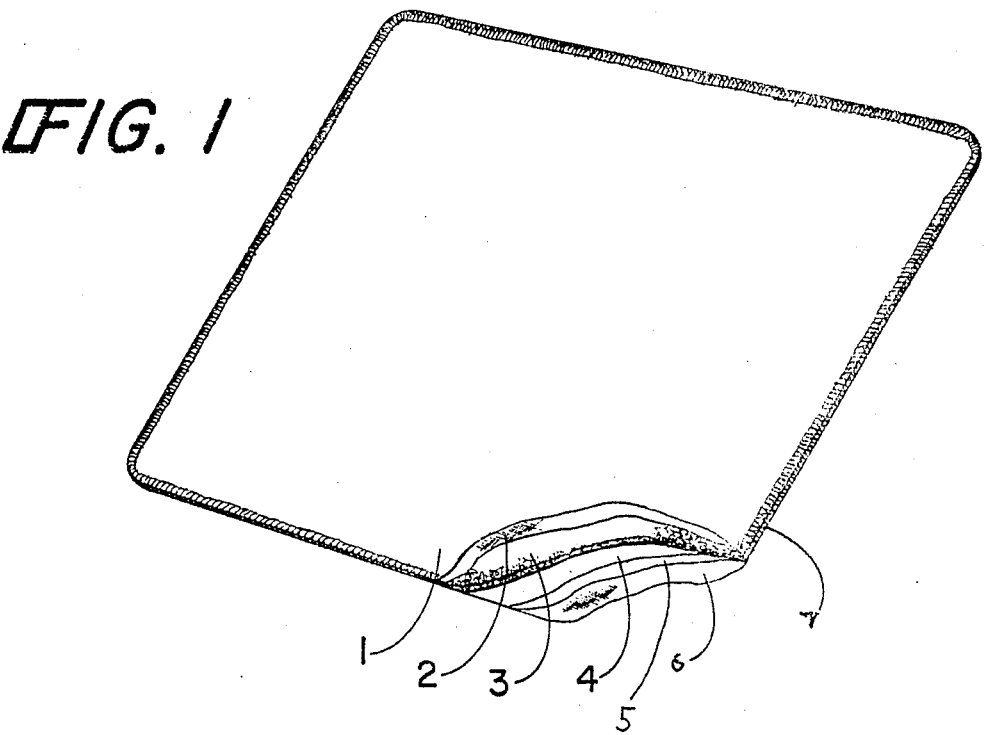
FIG. 1 is a perspective view of the underpad with a partial cut-away and cross-section showing the various fabric layers.

While the size and thickness of the pad can vary according to the precise needs of the user, the preferred embodiment shown in the drawings demonstrate the novel combination of fabrics and bonding which give the present invention its advantages and durability, comfort, and ease in use.

Figure 2:
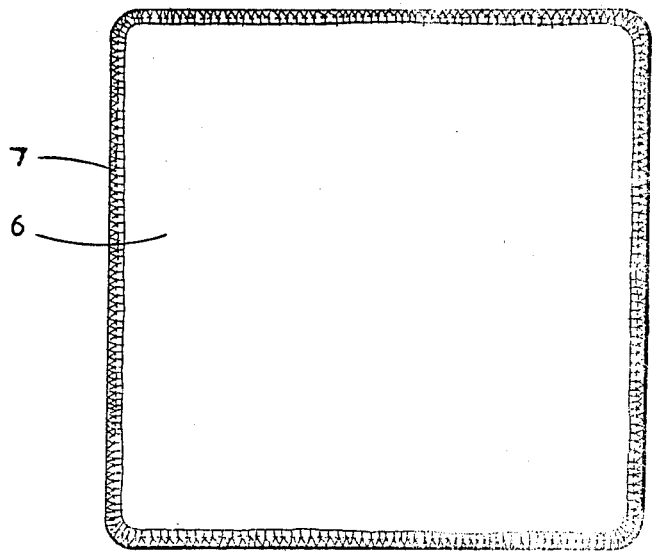
FIG. 2 is a bottom view of the pad showing the smooth bottom layer and the stitching around the edges of the pad.

As shown in FIGS. 1 and 2, the underpad is formed of a top layer of polyester-rayon needle form non-woven fabric that is run through an iron at a temperature of approximately 380 to 400 degrees F., to provide a smooth and comfortable surface for the patient. An example of this non-woven fabric is Style 700 from Chatman Manufacturing Co., Elkins, N.C. An acrylic-polyester-rayon fabric can also be used, using a heat set iron temperature closer to 300 degrees F. This particular fabric has four carded layers of fibers with the top layer 100% acrylic and the three succeeding layers comprising rayon-polyester fibers. The thickness of fabric layer 1 is chosen to accommodate the desired absorption needs of the pad.

Beneath layer 1 is fabric layer 2 of non-woven polyester which is not bonded to layer 1. Bonded across the lower surface of layer 2, by heat or glue is the water barrier layer of synthetic material. This synthetic material may be PVC, thermoplastic urethane, or other similar material. However, in the preferred embodiment, it has been found that a film of thermoplastic urethane ether offers improvements over PVC vinyl in its pliability and in its ability to resist heat and chemical attack. Further, it is also recognized that thermoplastic urethane ester is more resistant to chemical attack than thermoplastic urethane ether. Therefore, in the preferred embodiment, the water barrier layer is comprised of thermoplastic urethane ester film 3 bonded to thermoplastic urethane ether layer 4 which, in turn, is bonded to thermoplastic urethane ester film 5. Urethane layers 3, 4, and 5 are conventionally bonded using heated rollers. The bottom layer 6 is bonded by glue or heat across the bottom surface of layer 5. The bottom layer 6, which in use contacts the bedding, is made of a synthetic fleece warpknit fabric such as nylon or polyester to provide a smooth slidable surface for ease of moving or turning the patient while on the underpad.

All layers are bound together by stitching 7 around the top and bottom outside edges.

What I claim is:

1. An improved reusable patient underpad comprising:
   (a) a top absorbent layer of heat-treated polyester rayon needle form non-woven fabric;
   (b) a second layer of non-woven polyester;
   (c) a third layer of water impervious synthetic material, bonded to said second layer; and
   (d) a fourth layer of synthetic fleece warpknit fabric bonded to said third layer.

2. The underpad of claim 1 wherein said top layer is heat-treated to substantially 350 to 380 degrees F.

3. The underpad of claim 2 wherein said third layer is heat bonded to said second layer and said fourth layer by use of films of thermoplastic urethane ester.

4. The underpad of claim 3 wherein said third layer comprises thermoplastic urethane ether.

5. An improved reusable patient underpad comprising:
   (a) a top layer of absorbent acrylic-polyester-rayon needle form non-woven fabric heat treated to substantially 300 to 380 degrees F.;
   (b) a second layer of non-woven polyester;
   (c) a third layer of thermoplastic urethane ether;
   (d) a fourth layer of synethetic fleece warpknit;
   (e) wherein said third layer is heat-bonded to said second and fourth layers using films of thermoplastic urethane ester.

* * * * *